US009121893B2

(12) United States Patent
Schmand et al.

(10) Patent No.: US 9,121,893 B2
(45) Date of Patent: Sep. 1, 2015

(54) COMBINED PET/MR IMAGING SYSTEM AND APD-BASED PET DETECTOR FOR USE IN SIMULTANEOUS PET/MR IMAGING

(75) Inventors: Matthias J. Schmand, Lenoir City, TN (US); Ron Grazioso, Knoxville, TN (US); Ronald Nutt, Knoxville, TN (US); Robert E. Nutt, Knoxville, TN (US); Nan Zhang, Knoxville, TN (US); James Luke Corbeil, Knoxville, TN (US); Ralf Ladebeck, Erlamgen (DE); Markus Vester, Nürnberg (DE); Günter Schnur, Hemhofen (DE); Wolfgang Renz, Erlangen (DE); Hubertus Fischer, Bamberg (DE); Bernd J. Pichler, Scheyern (DE)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1074 days.

(21) Appl. No.: 11/532,665

(22) Filed: Sep. 18, 2006

(65) Prior Publication Data

US 2007/0102641 A1    May 10, 2007

Related U.S. Application Data

(63) Continuation of application No. 11/319,795, filed on Dec. 29, 2005.

(60) Provisional application No. 60/640,073, filed on Dec. 29, 2004, provisional application No. 60/738,998, filed on Nov. 23, 2005.

(51) Int. Cl.
*G01T 1/164*    (2006.01)
*G01T 1/166*    (2006.01)
(Continued)

(52) U.S. Cl.
CPC ............. *G01R 33/28* (2013.01); *A61B 6/037* (2013.01); *G01R 33/26* (2013.01); *G01R 33/381* (2013.01);
(Continued)

(58) Field of Classification Search
USPC ............... 250/363.03, 369; 600/407, 410
See application file for complete search history.

(56) References Cited

U.S. PATENT DOCUMENTS 4,939,464 A * 7/1990 Hammer .................. 324/318
6,054,705 A * 4/2000 Carroll ..................... 250/214 A
(Continued)

FOREIGN PATENT DOCUMENTS

DE    102005054227    5/2007
JP        7029489       1/1995
(Continued)

OTHER PUBLICATIONS

International Search Report including Notification of Transmittal of the International Search Report, International Search Report and Written Opinion of the International Searching Authority.
(Continued)

*Primary Examiner* — Joel F Brutus
(74) *Attorney, Agent, or Firm* — Peter Kendall

(57) ABSTRACT

APD-based PET modules are provided for use in combined PET/MR imaging. Each module includes a number of independent, optically isolated detectors. Each detector includes an array of scintillator (e.g. LSO) crystals read out by an array of APDs. The modules are positioned in the tunnel of a MR scanner. Simultaneous, artifact-free images can be acquired with the APD-based PET and MR system resulting in a high-resolution and cost-effective integrated PET/MR system.

9 Claims, 7 Drawing Sheets

(51) Int. Cl.
*G01R 33/28* (2006.01)
*G01R 33/26* (2006.01)
*G01R 33/381* (2006.01)
*G01R 33/48* (2006.01)
*G01T 1/16* (2006.01)
*G01T 1/29* (2006.01)
*A61B 6/03* (2006.01)
*A61B 8/08* (2006.01)

(52) U.S. Cl.
CPC ............ *G01R 33/481* (2013.01); *G01T 1/1603* (2013.01); *G01T 1/2985* (2013.01); *A61B 8/5261* (2013.01)

(56) References Cited

U.S. PATENT DOCUMENTS

| | | | |
|---|---|---|---|
| 6,946,841 | B2 | 9/2005 | Rubashov |
| 7,218,112 | B2 | 5/2007 | Ladebeck et al. |
| 2003/0090267 | A1 | 5/2003 | Rubashov |
| 2003/0105397 | A1* | 6/2003 | Tumer et al. ............... 600/436 |
| 2003/0194050 | A1* | 10/2003 | Eberhard et al. ............ 378/37 |
| 2003/0213913 | A1* | 11/2003 | Moyers et al. ............. 250/369 |
| 2004/0065838 | A1 | 4/2004 | Tumer |
| 2004/0159791 | A1* | 8/2004 | Hefetz ................. 250/363.03 |
| 2005/0082486 | A1 | 4/2005 | Schlyer et al. |
| 2005/0113667 | A1* | 5/2005 | Schlyer et al. ............. 600/411 |
| 2006/0293580 | A1 | 12/2006 | Ladebeck et al. |
| 2007/0055127 | A1 | 3/2007 | Ladebeck et al. |

FOREIGN PATENT DOCUMENTS

| | | |
|---|---|---|
| JP | 7333348 A | 12/1995 |
| JP | 9090043 A | 4/1997 |
| JP | 2001004752 A | 1/2001 |
| JP | 2004317300 A | 11/2004 |
| JP | 2004350942 | 12/2004 |
| WO | 2004111681 | 12/2004 |
| WO | 2006111869 | 10/2006 |
| WO | 2006119085 | 11/2006 |

OTHER PUBLICATIONS

Schlyer D et al: Development of a Simultaneous PET/MRI Scanner 2004 Nuclear Science Symposium Conference Record Oct. 16-22, 2004 Rome, Italy, 2004 IEEE Nuclear Science Symposium Conference Record (IEEE Cat. No. 04CH37604) IEEE Piscataway, NJ, USA, vol. 6, Oct. 16, 2004, p. 3419-3421.
Anonymous: "Combined MRI and SPECT/PET imaging system" Research Disclosure, Mason Publications, Hampshire, GB vol. 451, No. 68, Nov. 1, 2001.
Hammer B E et al: "Use of a Magnetic Field to Increase the Spatial Resolution of Positron Emission Tomography" Medical Physics, AIP, Melville, NY, US, vol. 21, No. 12, Dec. 1, 1994, pp. 1917-1920.
Grazioso et al: "APD-based PET detector for simultaneous PET/MR imaging" Molecular Imaging, MIT Press, US, vol. 4, Jan. 1, 2005, p. 391.
Supplementary European Search Report in EP Application No. 05855710 dated Feb. 17, 2011.
Office action dated Nov. 30, 2010 in Japanese Patent Application No. 2007-549575 (English translation attached).
Office action in JP Patent Application No. 2007-549575 dated May 17, 2011.
B. Pichler, et al., "Performance Test of a LSO-APD PET Module in a 9.4 Tesla Magnet", Nuclear Science Symposium, IEEE, vol. 2, 1237-1239, 1997.
European Patent Office Communication dated Mar. 5, 2013 for Patent Application No. 05855710.9.

* cited by examiner

COMBINED PET/MR IMAGING SYSTEM AND APD-BASED PET DETECTOR FOR USE IN SIMULTANEOUS PET/MR IMAGING

CLAIM OF PRIORITY FROM RELATED APPLICATIONS

This application is a continuation of application Ser. No. 11/319,795 filed Dec. 29, 2005, which claims priority under 35 U.S.C. §119(e) from provisional applications Ser. No. 60/640,073 filed Dec. 29, 2004, and Ser. No. 60/738,998 filed Nov. 23, 2005.

FIELD OF THE INVENTION

The present invention generally relates to the field of medical imaging, and systems for obtaining diagnostic images such as nuclear medicine images and magnetic resonance (MR) images. In particular, the present invention relates to multiple modality imaging systems and methods for obtaining diagnostic images of multiple modalities, such as nuclear medicine images from positron emission tomography (PET) data and magnetic resonance imaging (MRI) data. The PET images and MR images can be obtained either sequentially or simultaneously.

BACKGROUND OF THE INVENTION

Nuclear medicine is a unique medical specialty wherein radiation is used to acquire images which show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions which emanate from the body and are captured by a scintillation crystal, with which the photons interact to produce flashes of light or "events." Events are detected by an array of photodetectors, such as photomultiplier tubes, and their spatial locations or positions are calculated and stored. In this way, an image of the organ or tissue under study is created from detection of the distribution of the radioisotopes in the body.

One particular nuclear medicine imaging technique is known as Positron Emission Tomography, or PET. PET is used to produce images for diagnosing the biochemistry or physiology of a specific organ, tumor or other metabolically active site. Measurement of the tissue concentration of a positron emitting radionuclide is based on coincidence detection of the two gamma photons arising from positron annihilation. When a positron is annihilated by an electron, two 511 keV gamma photons are simultaneously produced and travel in approximately opposite directions. Gamma photons produced by an annihilation event can be detected by a pair of oppositely disposed radiation detectors capable of producing a signal in response to the interaction of the gamma photons with a scintillation crystal. Annihilation events are typically identified by a time coincidence between the detection of the two 511 keV gamma photons in the two oppositely disposed detectors, i.e., the gamma photon emissions are detected virtually simultaneously by each detector. When two oppositely disposed gamma photons each strike an oppositely disposed detector to produce a time coincidence event, they also identify a line of response, or LOR, along which the annihilation event has occurred.

An example of a PET method and apparatus is described in U.S. Pat. No. 6,858,847, which patent is incorporated herein by reference in its entirety. After being sorted into parallel projections, the LORs defined by the coincidence events are used to reconstruct a three-dimensional distribution of the positron-emitting radionuclide within the patient. PET is particularly useful in obtaining images that reveal bioprocesses, e.g. the functioning of bodily organs such as the heart, brain, lungs, etc. and bodily tissues and structures such as the circulatory system.

On the other hand, Magnetic Resonance Imaging (MRI) is primarily used for obtaining high quality, high resolution anatomical and structural images of the body. MRI is based on the absorption and emission of energy in the radio frequency range primarily by the hydrogen nuclei of the atoms of the body and the spatial variations in the phase and frequency of the radio frequency energy being absorbed and emitted by the imaged object. The major components of an MRI imager include a cylindrical magnet, gradient coils within the magnet, an RF coil within the gradient coil, and an RF shield that prevents the high power RF pulses from radiating outside of the MR imager, and keeps extraneous RF signals from being detected by the imager. A patient is placed on a patient bed or table within the magnet and is surrounded by the gradient and RF coils.

The magnet produces a $B_o$ magnetic field for the imaging procedure. The gradient coils produce a gradient in the $B_o$ field in the X, Y, and Z directions. The RF coil produces a $B_1$ magnetic field necessary to rotate the spins of the nuclei by 90° or 180°. The RF coil also detects the nuclear magnetic resonance signal from the spins within the body. A radio frequency source produces a sine wave of the desired frequency.

The concept of merging PET and MR imaging modalities into a single device is generally known in the art. See, e.g., U.S. Pat. No. 4,939,464, incorporated herein by reference in its entirety. The original ideas focused around transporting the light from scintillation crystals positioned inside the MR field of view, via optical guides such as lightpipes, to photomultiplier tube photodetectors positioned outside of the magnetic field. This was necessary because the photomultiplier tubes are sensitive to magnetic field disturbance. However, such designs have not been able to achieve high performance characteristics and suffer from complicated design requirements.

SUMMARY OF THE INVENTION

The present invention overcomes the problems in the prior art, by providing an APD-based (Avalanche PhotoDiode) PET detector with a MR scanner. Because APDs are quite small and are magnetically insensitive, a detector could be designed that could fit into the tunnel of the MR scanner either as a removable insert for head and extremity imaging, or could be fully integrated into the MR scanner itself.

BRIEF DESCRIPTION OF THE DRAWINGS

The invention will now be more fully described by way of example with reference to the accompanying drawings in which:

FIG. 7 is a composite diagram showing $^{22}$Na energy spectra and position profile of one block in a PET detector module in accordance with the invention, with the MR RF sequence on;

DETAILED DESCRIPTION OF THE INVENTION

The present invention will now be described and disclosed in greater detail. It is to be understood, however, that the disclosed embodiments are merely exemplary of the invention and that the invention may be embodied in various and alternative forms. Therefore, specific structural and functional details disclosed herein are not to be interpreted as limiting the scope of the claims, but are merely provided as an example to teach one having ordinary skill in the art to make and use the invention.

Figure 1:
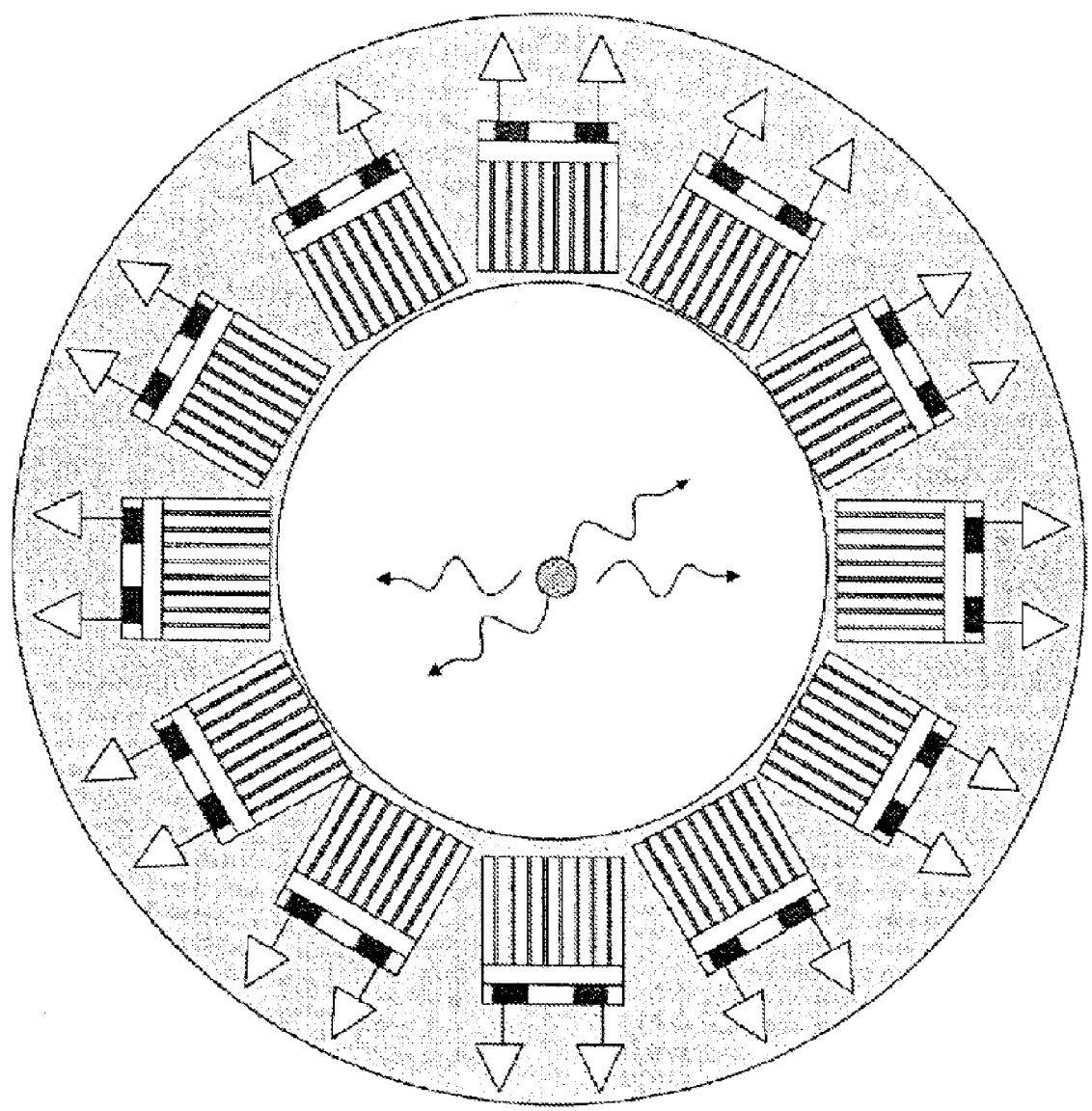
FIG. 1 is a diagram of a PET detector ring in accordance with an embodiment of the invention.
Figure 2:
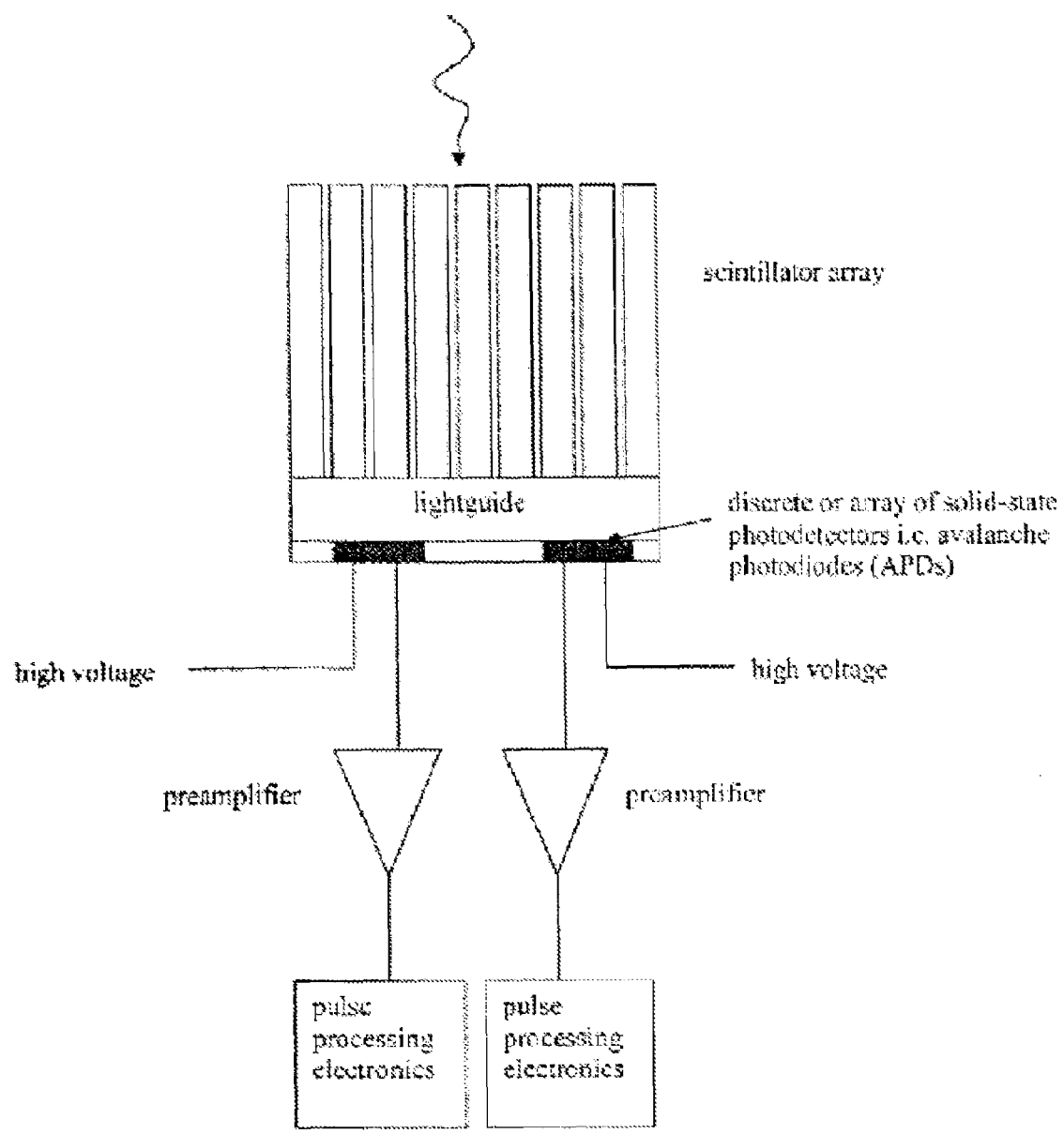
FIG. 2 is a circuit block diagram of the components of a detector module as incorporated in FIG. 1.

As shown in FIG. 1, a PET scanner in accordance with one embodiment of the invention includes a plurality of detector modules arranged in a ring configuration. As shown in FIG. 2, each detector module includes a scintillator block that is optically coupled through a light guide to a solid state photodetector or array of photodetectors, such as avalanche photodiodes (APDs) or other semiconductor-based type of photodetector. For purposes of explanation, the example of using APDs will be discussed hereinafter.

Each individual solid-state photodetector may be optically coupled to more than one scintillator, or may be coupled in a one-to-one scintillator to photodetector arrangement. Each APD is electrically connected to a high voltage source. Multiple APDs may share a single voltage source. The charge created in the APDs is collected in a preamplifier, such as a charge-sensitive preamplifier, transimpedance preamplifier or voltage-sensitive preamplifier. The pulse signals produced by the preamplifiers are then inputted to appropriate pulse processing electronics, as generally known in the art.

Figure 3:
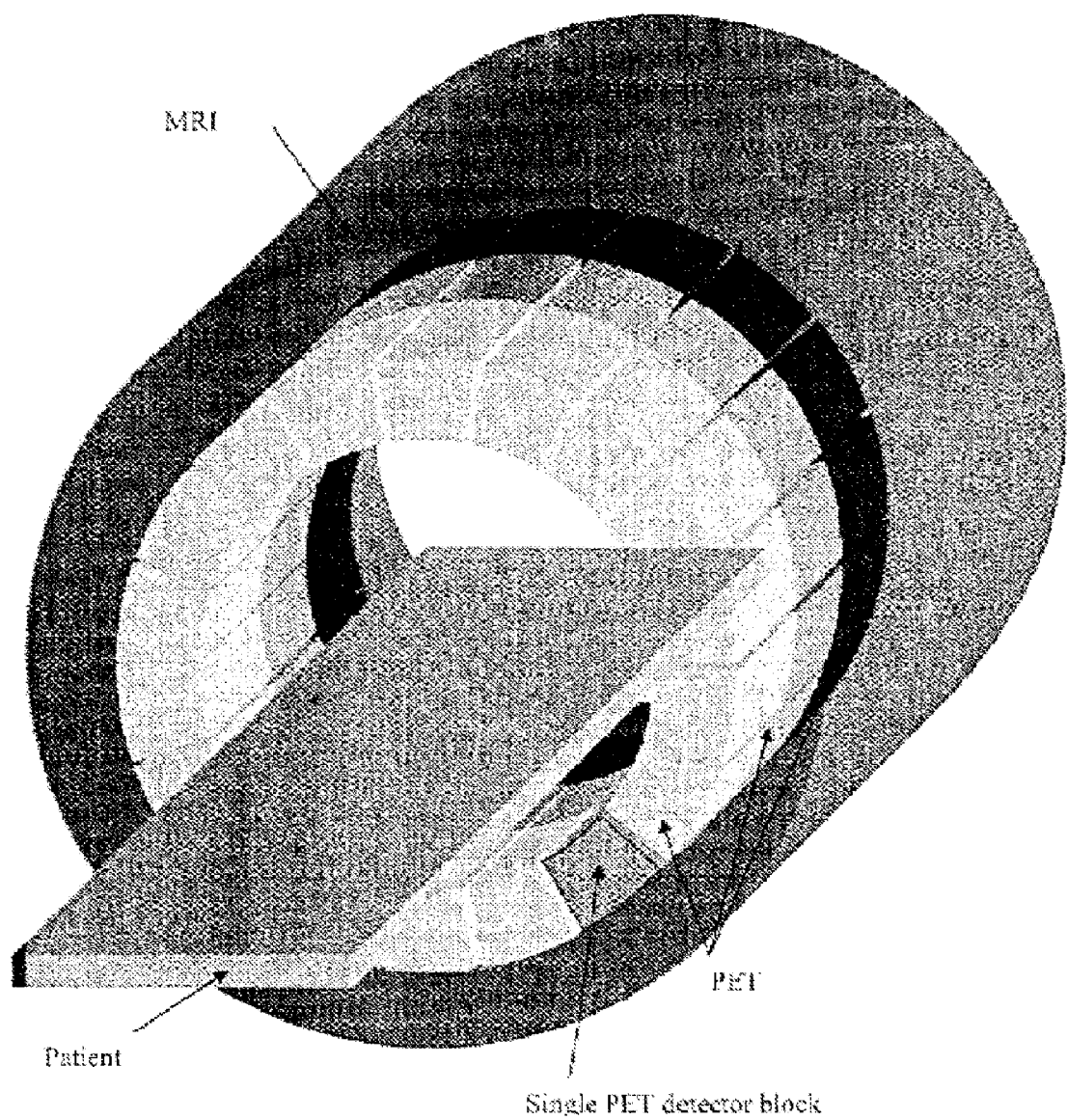
FIG. 3 is a perspective view of a combined PET/MR system in accordance with an embodiment of the invention, showing a plurality of PET detector rings within an MR field of view.

FIG. 3 illustrates one possible embodiment of the invention wherein a plurality of PET detector rings, such as 3, are disposed within an MRI magnet. Accordingly, each detector ring has an outer diameter dimensioned to be received within the geometry of the MRI scanner. The number of PET detector rings may more than 3 or less than 3, and in a particular alternate embodiment a single PET detector ring may be provided. A patient table or bed is provided to receive a patient to be imaged. PET and MR data acquisitions are carried out on the patient, either simultaneously, in an interlaced or interleaved manner, or sequentially.

Figure 4:
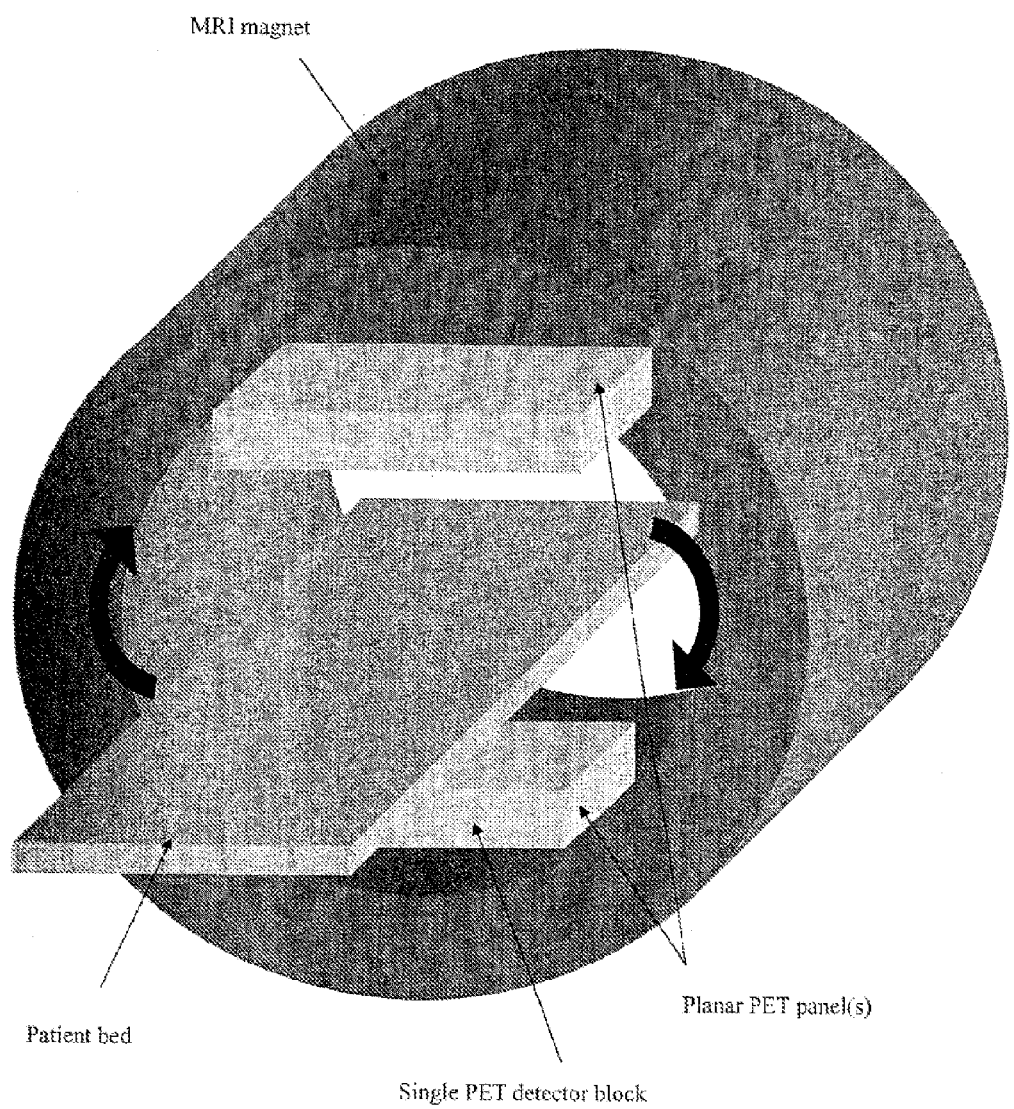
FIG. 4 is a perspective view of a combined PET/MR system in accordance with another embodiment of the invention, showing a plurality of planar PET detector panels positioned on the end of a MR scanner.

An additional alternate embodiment of the invention is shown in FIG. 4, wherein two planar PET detector panels are provided and positioned 180° apart within the MR scanner FOV. The PET detector panels also may be positioned at the end of the MR patient gantry outside the FOV. While two panels are shown in the example embodiment of FIG. 4, it will be recognized that more than two detector panels may be provided in various alternative configurations. The detector panels may be configured to rotate about the patient, either partially or a full 360°. The detector panels also may be configured to be stationary. In each of the embodiments, the PET detector modules can be either permanently mounted within or on the MRI scanner, or be retractable therefrom.

Example Implementation and Test Measurement

Figure 5:
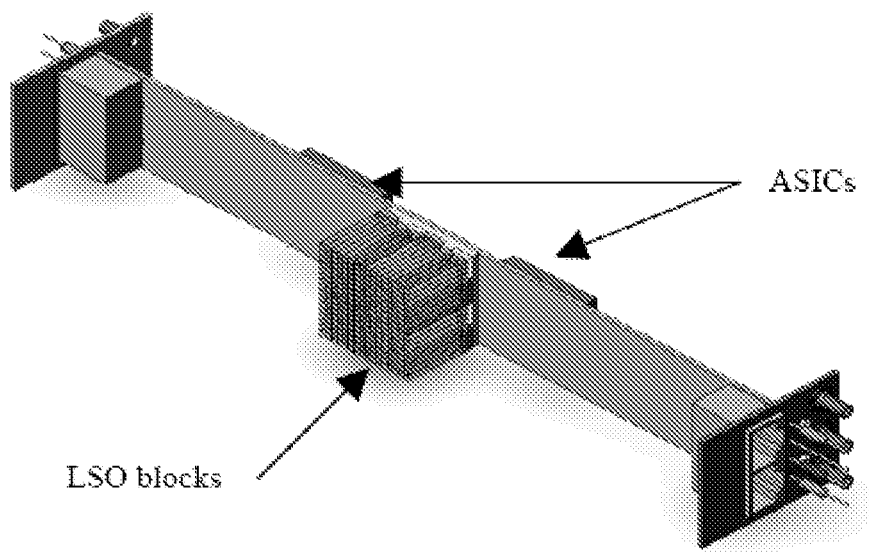
FIG. 5 is a perspective view of a PET detector module in accordance with another embodiment of the invention.

An APD-based PET module has been built and tested for use in a MR scanner for simultaneous PET/MR imaging according to the present invention. The module consisted of 4 optically isolated scintillator blocks each read out by a 2×2 APD array, as shown in FIG. 5. One basic APD detector design according to an embodiment of the invention is based on an LSO block design. The scintillator blocks are 8×8 arrays of 2 mm×2 mm×20 mm LSO crystals coupled to glass light guides. The APDs are coupled to the glass light guides. The APDs can be any commercially available APD, such as, e.g., Hamamatsu S8664-55 APDs in a custom package, or APDs available from Perkin-Elmer. The APD signals are amplified by a charge-sensitive preamplifier ASIC, and shaped by a pole-zero circuit. Therefore one module contained 4 LSO blocks, 16 APDs, 2 ASIC preamplifiers, and 16 channels of pole-zero electronics.

Figure 6:
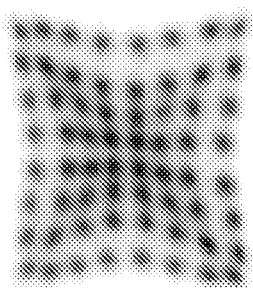
FIG. 6 is a position profile of a readout of the detector as shown in FIG. 5.

The outputs of the modules were sampled and digitized by Siemens Pico3D electronics, which determine energy, timing and position. A typical position profile is shown in FIG. 6. The average crystal time resolution (against a plastic scintillator on a PMT) was 1.8 ns, while the average crystal energy resolution was 17%.

Each module was packaged in a box made of copper-coated FR-4 board. The FR-4 board had a 10 μm (⅛ oz.) thick copper coating for RF shielding. The output signal cables were 7 m long, twisted-pair cables with an RJ45 connector. All of the cables were connected to a feed-through plate mounted to the wall in the RF-shielded MR room. The power supplies and Pico3D electronics were in a technical room on the other side of the feed-through plate. This ensured that the MR electronics were shielded from the PET electronics and vice versa. The modules were mounted on a RF shielded gantry that was positioned inside the tunnel of a Siemens Symphony 1.5 Tesla MR scanner. A transmit/receive head coil was placed in the center of the gantry.

A 22Na source was used for setup and compatibility measurements. For simultaneous imaging, a small Derenzo phantom (32 mm diameter and 16 mm tall) with holes ranging from 1.0 mm to 3.5 mm in 0.5 mm increments was placed in a rotational holder. The phantom could be rotated in 19 steps for 180° rotation to allow 3D imaging. The phantom was filled with water and 1.25 g NiSO4/liter (as an MR contrast agent) and about 50 MBq FDG.

Measurements were performed to determine the effects the PET modules had on the MR performance as well as the effect the magnetic field, RF and gradient pulses had on the PET performance. While the PET modules were acquiring data; MR sequences were being performed to quantify the effect the PET modules had on the MR image. Baseline MR images were acquired with the PET modules in and out of the MR scanner. When the PET modules were inside the MR tunnel, the signal-to-noise ratio of the MR decreased by 15%. Thus, this effect could be reduced by using improved shielding of the PET modules and cables.

Spikes are RF signals with a broadband RF spectrum generated, e.g., by electrostatic discharges. Spikes can produce a high background noise level or a sine wave artifact in the image. No spikes were observed in the MR baseline image. An MR head phantom image was acquired with the PET modules in place. Any magnetic components close to the phantom would introduce distortion artifacts in the phantom image. No interference was seen due to the PET modules or gantry, as all of the components are non-magnetic or far enough away from the phantom to eliminate any significant interference.

With the PET modules acquiring data, the MR scanner transmitted varying degrees of gradient and RF pulse sequences. The APD output signals and CFD trigger were observed on an oscilloscope to see the effects. Position profile and energy spectra data were also acquired during gradient and RF pulse sequencing. Static magnetic field measurements were performed to determine the effects the PET modules had on the MR performance as well as the effect that the magnetic field, RF and gradient pulses had on the PET performance. There was no observable effect from the static magnetic field of the MR scanner.

A gradient sequence was set to 20 mT/m with a ramp time of 0.1 ms and a 2 ms repetition time. The gradient pulses were bipolar with no top and were transmitted in all 3 directions. This is a very aggressive sequence with respect to generating as much induction as possible by the MR scanner. This sequence was transmitted for 20 minutes. The detector was placed in the region of maximum flux density. The gradient pulses were observed in the output signals from the detector modules using an oscilloscope. But the gradient pulses did not trigger the CFD and therefore were not seen in the energy spectra and position profile. However, the gradient pulses did block the true event signals, effectively increasing the dead time of the system. This effect could be reduced by minimizing ground loops within the PET system.

Figure 7:
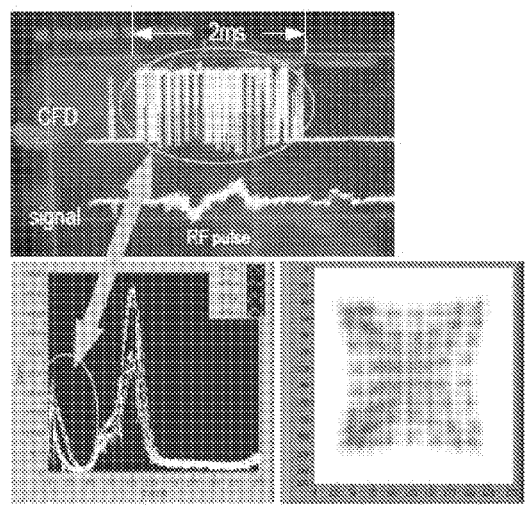

A RF sequence was transmitted with an amplitude of 730 V, a pulse width of 1 ms and a repetition time of 10 ms. This corresponds to a B1 flux density of about 30 µT. Again, this is an aggressive sequence for the MR scanner. This sequence was transmitted for 10 minutes. The RF pulses were observed in the output signals from the detector modules using an oscilloscope. But unlike the gradient pulses, the RF pulses did trigger the CFD and therefore were seen in the energy spectra. However, the RF pulses created low energy counts in the energy spectra and therefore did not affect the 511 keV photopeak. Due to the normal system energy gating of the PET electronics, the effect of the RF pulses was not seen in the position profile as shown in FIG. 7. But the RF pulses would also increase the dead time of the PET system. Better RF shielding could help reduce this effect.

PET and MR images were acquired simultaneously to show proof-of-principle compatibility for an integrated system. The PET image was acquired using a step-and-shoot method. PET data were acquired with the Derenzo phantom for each of 19 rotational positions. The PET acquisition time ranged from 6 min. for the first step to 21 min. for the last step (in order to correct for the FDG half-life). For each of the 19 phantom positions, an MR image was acquired using a spin echo sequence followed by a 2D gradient echo sequence and a 3D gradient echo sequence for a total acquisition time of 5 min. The PET image was reconstructed using all of the positions.

Figure 8:
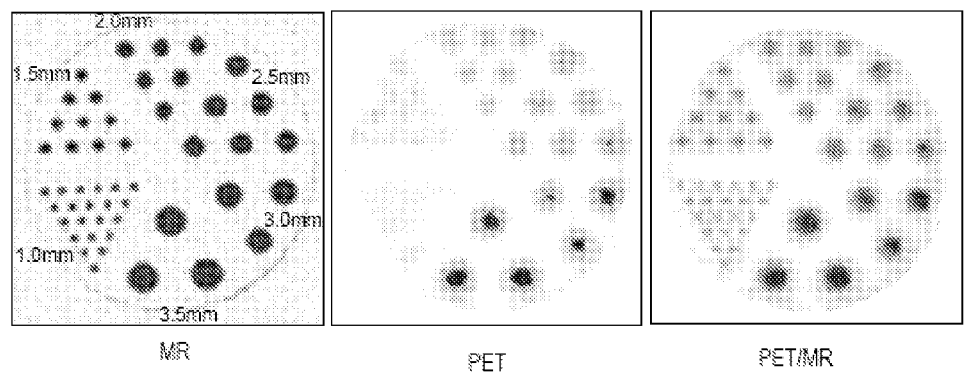
FIG. 8 shows respective MR, PET and fused PET/MR images of a Derenzo phantom acquired in accordance with a combined PET/MR system of the present invention.
Figure 9:
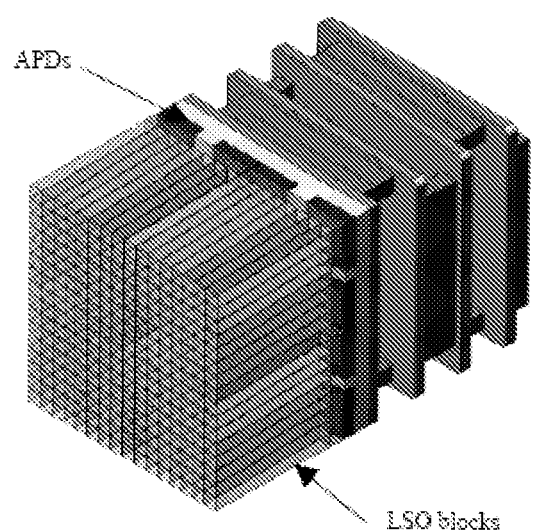
FIG. 9 is a perspective diagram of stacked-board APD detector design in accordance with the invention, to fit in the tunnel of an MR scanner for brain imaging.

The MR, PET and fused images are shown in FIG. 8. The images show no artifacts. All of the holes can be clearly seen in the MR image and the smallest holes visible in the PET image are the 2 mm holes. These measurements demonstrate the benefits of an integrated APD-based PET/MR scanner in accordance with the invention. Simultaneous PET and MR imaging is achievable without any image artifacts or distortion. An alternate modular APD detector for a PET/MR brain scanner can be based on a stacked board design in order to fit into the tight space constraints of the MR tunnel, as shown in FIG. 9.

It should be appreciated by those having ordinary skill in the art that while the present invention has been illustrated and described in what is deemed to be the preferred embodiments, various changes and modifications may be made to the invention without departing from the spirit and scope of the invention. Therefore, it should be understood that the present invention is not limited to the particular embodiments disclosed herein.

What is claimed is:

1. A combined positron emission tomography (PET) and magnetic resonance imaging (MRI) apparatus, comprising:
    an MR scanner including a magnet for generating a magnetic field for inducing NMR signals from nuclei of a subject to be imaged within a field of view of said MR scanner; and
    a PET detector module including a scintillator and a solid-state photodetector having a photodecting surface optically coupled to said scintillator, said PET detector module being retractably disposed within said magnetic field, both sais scintillator and said solid-state photodetector being disposed within said magnetic field with said photodetecting surface being fixed parallel to said magnetic field;
    wherein said solid-state photodetector is a silicon-based photodetector.

2. A combined PET and MRI apparatus as set forth in claim 1, further including a plurality of said PET detector modules arranged in a ring configuration within said magnetic field.

3. A combined PET and MRI apparatus as set forth in claim 2, further including a plurality of ring configurations disposed within said magnetic field.

4. A combined PET and MRI apparatus as set forth in claim 1, wherein said scintillator is an LSO crystal.

5. A combined PET and MRI apparatus as set forth in claim 1, further comprising a preamplifier for collecting an electric charge generated by said solid-state photodetector in response to scintillation events.

6. A combined PET and MRI apparatus as set forth in claim 5, wherein said preamplifier is selected from the group consisting of a charge sensitive preamplifier, a transimpedance preamplifier, and a voltage sensitive preamplifier.

7. A combined PET and MRI apparatus as set forth in claim 1, wherein said PET detector module is a planar PET detector panel, and further including at least a pair of said planar PET detector panels spaced apart by 180°.

8. A combined positron emission tomography (PET) and magnetic resonance imaging (MRI) apparatus, comprising:
    an MR scanner including a magnet for generating a magnetic field for inducing NMR signals from nuclei of a subject to be imaged within a field of view of said MR scanner; and
    a PET detector module including a scintillator and a solid-state photodetector having a photodetecting surface optically coupled to said scintillator, and PET detector module being disposed within said magnetic field, both said scintillator and said solid-state photodetector being disposed within said magnetic field with said photodetecting surface being parallel to said magnetic field,
    wherein outputs of the PET module are sampled and digitized outside of the magnetic field.

9. A combined positron emission tomograghy(PET) and magnetic resonance imaging (MRI) apparatus, comprising:

an MR scanner including a magnet for generating a magnetic field for inducing NMR signals from nuclei of a subject to be imaged within a field of view of said MR scanner; and a PET detector module including a scintillator and a solid-state photodetector having a photodetecting surface optically coupled to said scintillator, said PET detector module being disposed within said field of view, both said scintillator and said solid-state photodetector being disposed within the said field of view with said photodetecting surface being parallel to said magnetic field, wherein outputs of the PET module are sampled and digitized outside of the magnetic field.

* * * * *